(12) United States Patent
Chen

(10) Patent No.: US 10,369,059 B2
(45) Date of Patent: Aug. 6, 2019

(54) DISPOSABLE HYGIENE ARTICLE COMPRISING A MELT-SPUN ELASTIC FIBER

(71) Applicant: BASF SE, Ludwigshafen (DE)

(72) Inventor: Bin-Erik Chen, Shanghai (CN)

(73) Assignee: BASF SE, Ludwigshafen (DE)

( * ) Notice: Subject to any disclaimer, the term of this patent is extended or adjusted under 35 U.S.C. 154(b) by 386 days.

(21) Appl. No.: 15/029,135

(22) PCT Filed: Oct. 7, 2014

(86) PCT No.: PCT/EP2014/071401
§ 371 (c)(1),
(2) Date: Apr. 13, 2016

(87) PCT Pub. No.: WO2015/055459
PCT Pub. Date: Apr. 23, 2015

(65) Prior Publication Data
US 2016/0256334 A1    Sep. 8, 2016

(30) Foreign Application Priority Data
Oct. 14, 2013 (WO) ................ PCT/CN2013/085161

(51) Int. Cl.
*A61F 13/15* (2006.01)
*A61F 13/49* (2006.01)

(52) U.S. Cl.
CPC .... *A61F 13/4902* (2013.01); *A61F 13/15593* (2013.01)

(58) Field of Classification Search
CPC ................ A61F 13/4902; A61F 13/15593
USPC ................... 604/360, 366, 367, 370
See application file for complete search history.

(56) References Cited

U.S. PATENT DOCUMENTS

| 4,968,313 A | 11/1990 | Sabee |
| 6,437,014 B1 | 8/2002 | Ho et al. |
| 2002/0147273 A1 | 10/2002 | Patel et al. |
| 2002/0161159 A1* | 10/2002 | Vedula .................... C08L 75/08 528/44 |
| 2003/0060529 A1 | 3/2003 | Ho et al. |
| 2004/0230012 A1 | 11/2004 | Vedula et al. |
| 2011/0123775 A1* | 5/2011 | Westwood ........... D04H 1/4382 428/172 |

FOREIGN PATENT DOCUMENTS

| WO | 01/85843 A1 | 11/2001 |
| WO | 2004/092241 A1 | 10/2004 |
| WO | WO 2009/008602 A1 | 1/2009 |
| WO | 2010/125009 A1 | 11/2010 |

OTHER PUBLICATIONS

International Search Report and Written Opinion dated Nov. 17, 2014 for PCT/EP2014/071401 filed on Oct. 7, 2014.
"Plastics Additives Handbook" Edited by Dr. Hans Zweifel, Hanser Publishers, Munich, 5$^{th}$ Edition, 2001, 29 Pages.
David F. Cadogan, et al., "Plasticizers" Ullmann's Encyclopedia of Industrial Chemistry, Wiley-VCH Verlag GmbH & Co. KGaA, Weinheim, vol. 27, 2012, pp. 600-618 (with Cover Page).

* cited by examiner

*Primary Examiner* — Jacqueline F Stephens
(74) *Attorney, Agent, or Firm* — Oblon, McClelland, Maier & Neustadt, L.L.P.

(57) ABSTRACT

The present invention relates to a disposable hygiene article comprising a melt-spun elastic fiber, in particular a diaper. Furthermore, the present invention relates to a process for preparing a disposable hygiene article comprising the steps of providing a melt-spun elastic fiber and applying the melt-spun elastic fiber to a disposable hygiene article or a part which is used to prepare the disposable hygiene article; as well as the use of a melt-spun elastic fiber in a preparation process for preparing a disposable hygiene article.

14 Claims, No Drawings

DISPOSABLE HYGIENE ARTICLE COMPRISING A MELT-SPUN ELASTIC FIBER

CROSS-REFERENCE TO RELATED APPLICATIONS

This application is a National Stage of PCT/EP2014/071401, which was filed on Oct. 7, 2014. This application is based upon and claims the benefit of priority to PCT/CN2013/085161, which was filed on Oct. 14, 2013.

BACKGROUND OF THE INVENTION

The present invention relates to a disposable hygiene article comprising a melt-spun elastic fiber, in particular a diaper. Furthermore, the present invention relates to a process for preparing a disposable hygiene article comprising the steps of providing a melt-spun elastic fiber and applying the melt-spun elastic fiber to a disposable hygiene article or a part which is used to prepare the disposable hygiene article; as well as the use of a melt-spun elastic fiber in a preparation process for preparing a disposable hygiene article.

Disposable hygiene articles are increasingly used because of their convenience. A disposable diaper, for example, varies from baby diaper to adult diaper in its size, usability and shape. Recently, a pull-up type in a form of short pants is more widely used than a simple straight diaper. An elastic body is used for this type of disposable diaper for elasticity and wearing comfort. A rubber-based elastic yarn or a polyurethane-based dry spun spandex fiber is widely used, mainly on the flap part of the legs and the cuff part, and stretchable nonwoven fabric is used on the side panels and on the waist band. The flap part of the legs and the cuff part have impact on the functionality and wearing comfort of diapers, depending on the physical properties of elastic yarns used. And diaper manufacturers are now making ceaseless efforts to develop an elastic yarn having improved flexibility as well as wearing comfort in order to produce a higher value-added diaper.

The cuff part in disposable diapers primarily prevents the liquid discharge from leaking out and the flap part of the legs secondly prevents leakage of the liquid discharge. These two parts have direct influence on wearing comfort as they are closely attached to the body. If the elastic yarn used is too tight, it leads to deterioration in wearing comfort, and causing red mark around the legs, whereas if too loose, the liquid discharge would leak out of the diaper. That is, if the elastic yarn too much extended is applied to the diaper in order to prevent the liquid discharge from leaking outside, it can increase the tightness of the elastic yarn, but lead to uncomfortable wearing, and causing red mark and pain on the skin. On the other hand, if an elastic yarn relatively less extended is applied to the diaper, the wearing comfort would be improved, but causing a problem of leaking. Therefore, in order to improve both the functionality and wearing comfort, an elastic yarn is required to be flexible enough to extend easily when being pulled, and to be closely attached to the body all the time. This relates closely to power retention of an elastic yarn.

Among the conventional elastic yarns, a rubber-based elastic yarn has the best functionality and wearing comfort. A rubber-based elastic yarn has high power retention of 70% to 80% so that it has better wearing comfort and functionality than any other elastic yarns used before. It has drawbacks, however, in that the process quality is relatively inferior to that of a spandex fiber due to a yarn cutting during the production of diapers, and has a poor tolerance to chemicals. In terms of economic feasibility, the price per unit weight of rubber-based elastic yarn is lower compared to a spandex fiber, but in effect, the amount of rubber-based elastic yarn used to make one diaper is more than three times that of a spandex fiber, so in practice when making one diaper, using a rubber-based elastic yarn is less economical than using a spandex fiber.

Meanwhile, most of the dry spun spandex fibers used in disposable hygiene articles such as diapers or sanitary napkins are unable to achieve both the wearing comfort and functionality at the same time, since they have power retention of less than 65%. That is, in case that an elastic yarn is applied loosely to improve wearing comfort, the possibility of leakage of liquid discharge increases, while an elastic yarn is applied tightly in order not to cause leakage, the tightness is such great that it leads to red mark on the skin.

Furthermore, dry spun spandex fibers are potentially harmful and might cause skin irritation due to remaining solvents which are used in the preparation process and cannot be completely removed from the resulting fiber. In the recent public consultation (RCOM, 2012), the average DMAc residues reported herein for raw fibers (0.1-0.5%) were basically confirmed. This is disadvantageous for hygiene articles which come in direct contact with the skin, in particular when used for babies.

Therefore, it was an object of the present invention to provide hygiene articles which avoid the use of potentially harmful dry spun spandex fibers. At the same time it was desirable to obtain hygiene articles which have similar properties to those prepared using dry spun spandex fibers or rubber-based fibers.

Another object of the present invention was to provide disposable hygiene articles which can be prepared in an efficient manner.

These objects of the invention are achieved by a disposable hygiene article comprising a melt-spun elastic fiber.

BRIEF SUMMARY THE INVENTION

If a melt-spun elastic fiber is applied to disposable hygiene articles such as a diaper or sanitary napkins, products can be produced with functionality and wearing comfort, while the problem of the presence of potentially harmful substances is avoided. The liquid discharge may be held inside the pad of a diaper and at the same time making a user feel fine and comfortable.

Melt-spun elastic fibers not only provide comparable quality as dry spun spandex, but the production process is more environmentally-friendly enabling a more energy saving process and a safer manufacturing environment as well as the safer use of melt-spun elastic fibers. In the process for preparing melt-spun elastic fibers, no solvent is used and none of the raw materials contains any solvent. Therefore the resulting fibers do not contain potentially harmful solvent residues.

Generally, all suitable melt-spun elastic fibers can be used, for example melt-spun elastic fibers based on thermoplastic polyurethanes (TPU) or melt-spun elastic fibers based on other thermoplastic elastomers such as thermoplastic polyester-ethers (TPEE), styrene butadiene based polymers (SBS), thermoplastic polyolefins (TPO) and polyether block amides (PEBAX).

In particular melt-spun elastic fibers based on thermoplastic polyurethanes are advantageous for the use in disposable hygiene articles, in particular in diapers. The fibers are prepared in a solvent free process. Furthermore, the fibers have good mechanical properties, for example high elongation at break, high abrasion resistance and good hydrolysis resistance.

For example melt-spun elastic fibers made from Elastollan® TPU meet the requirements of Oeko-Tex® Standard 100, which is a global testing and certification system for screening harmful and restricted substances in consumer textile products. The results of the inspection according to Oeko-Tex® Standard 100 have shown that the Elastollan® melt-spun elastic fibers meet class I (baby articles) of the present human-ecological requirement standards.

It has surprisingly been found that high linear density melt-spun elastic fibers which are generally not used for other applications, such as hosiery and stocking, can be used in the preparation of disposable hygiene articles, in particular in diapers. The resulting disposable hygiene articles do not contain potentially harmful solvent residues unlike those which are prepared using dry spun spandex fibers.

According to a further embodiment the present invention therefore is directed to a disposable hygiene article as disclosed above, wherein the melt-spun elastic fiber is based on a thermoplastic polyurethane.

DETAILED DESCRIPTION OF THE INVENTION

A melt-spun elastic fiber in the context of the present invention can be characterized by the IR-spectrum of the compound. In contrast to a dry spun fiber which shows a characteristic signal at 1630 cm$^{-1}$, the melt-spun elastic fiber has no signal in the range of from 1620 cm$^{-1}$ to 1640 cm$^{-1}$.

If not noted otherwise, the wave length refers to a FT IR-spectrum measured at a wave length in the range of 4000 to 600 cm$^{-1}$.

According to the present invention, fibers with any suitable linear density can be used. For example, the linear density might be in the range of from 200D to 1000D. It has been found advantageous to use fibers with a linear density in the range of from 200D to 800D or in the range of from 800D to 1000D. More preferred, the linear density is in the range of from 400D to 600D, for example 450D, 500D or 550D or in the range of from 850D to 1000D, such as from 900D to 1000D, for example 950D.

Denier (unit "D" or also "den") is a unit of measurement that is used to determine the fiber linear density of individual threads or filaments, 1D means a 9000 m long fiber has 1 g weight. The linear density of the fibers is measured according to DIN 53830.

According to a further embodiment the present invention therefore is directed to a disposable hygiene article as disclosed above, wherein the melt-spun elastic fiber has a linear density in the range of from 200D to 800D.

According to an alternative embodiment the present invention therefore is directed to a disposable hygiene article as disclosed above, wherein the melt-spun elastic fiber has a linear density in the range of from 800D to 1000D.

The properties of the melt-spun elastic fibers or the thermoplastic polyurethane used for the preparation of the preferred melt-spun elastic fibers can vary in a broad range as long as the fibers are suitable for the preparation of disposable hygiene articles.

It has been found advantageous to use a thermoplastic polyurethane with a shore hardness in the range of from 60 A to 98 A, determined according to DIN 53505. The shore hardness preferably is in the range of from 70 A to 90 A, most prefer from 75 A to 85 A, in each case determined according to DIN 53505.

According to a further embodiment the present invention therefore is directed to a disposable hygiene article as disclosed above, wherein the thermoplastic polyurethane has a shore hardness in the range of from 60 A to 98 A, determined according to DIN 53505.

Melt-spun elastic fibers based on thermoplastic polyurethanes with a shore hardness in the range of from 60 A to 98 A, determined according to DIN 53505, are advantageous since this hardness allows for a good combination of physical properties for processing the resulting melt-spun elastic fibers. The resulting fibers are soft and comfortable but not too sticky.

The melt-spun elastic fiber has to be stable under normal use conditions and it has to be stable under the conditions of the preparation process of the disposable hygiene article Furthermore, the fibers have to be stable towards chemicals used in the preparation process of the disposable hygiene article and should be stable towards hydrolysis. Generally, the kofler melting temperature of melt-spun elastic fibers used in the context of the present invention is in the range of from 50° C. to 230° C., preferably in the range from 100° C. to 200° C., in particular from 150° C. to 200° C.

According to a further embodiment the present invention therefore is directed to a disposable hygiene article as disclosed above, wherein the melt-spun elastic fiber has a kofler melting temperature in the range of from 50° C. to 230° C.

Melt-spun elastic fibers based on thermoplastic polyurethanes generally are prepared using a cross linker. Suitable cross linkers are known from the state of the art. Melt-spun elastic fibers based on a thermoplastic polyurethane which are prepared using a cross linker comprising isocyanate groups are particularly suitable in the context of the present invention. Further compounds such as additives and plasticizers can be used to modify the properties of the resulting melt-spun elastic fibers.

According to a further embodiment the present invention therefore is directed to a disposable hygiene article as disclosed above, wherein the melt-spun elastic fiber is based on a thermoplastic polyurethane and a cross linker comprising isocyanate groups.

Melt-spun elastic fibers based on a thermoplastic polyurethane and a cross linker comprising isocyanate groups are generally known. Suitable thermoplastic polyurethanes and cross linkers are also known from the state of the art.

A suitable thermoplastic polyurethane which can be used for the preparation of melt-spun elastic fibers in the context of the present invention may comprise
  (a) one or more organic diisocyanates,
  (b) one or more compounds reactive toward isocyanate,
  (c) one or more chain extenders, preferably having a molecular weight of from 60 g/mol to 499 g/mol, and
  (d) optionally at least one catalyst, and/or
  (e) optionally at least one auxiliary, and/or
  (f) optionally at least one additive.

A suitable thermoplastic polyurethane for example has a number average molecular weight in the range of from 8*10$^4$ g/mol to 1.8*10$^5$ g/mol, more preferably in the range of from 1.0*10$^5$ g/mol to 1.5*10$^5$ g/mol.

The components (a), (b), (c) and optional components (d), (e) and (f) are generally known from the state of the art and are described by way of example in the following.

Suitable organic diisocyanates (a) are customary aliphatic, cycloaliphatic, araliphatic and/or aromatic isocyanates. Examples thereof include but are not limited to trimethylene diisocyanate, tetramethylene diisocyanate, pentamethylene diisocyanate, hexamethylene diisocyanate, heptamethylene diisocyanate and/or octamethylene diisocyanate, 2-methylpentamethylene 1,5-diisocyanate, butylenes 1,4-diisocyanate, 2-ethylbutylene 1,4-diisocyanate, pentamethylene 1,5-diisocyanate, 1-isocyanato-3,3,5-trimethyl-5-isocyanatomethylcyclohexane (isophorone diisocyanate, IPDI), 1,4- and/or 1,3-bis(isocyanatomethyl)cyclohexane (HXDI), cyclohexane 1,4-diisocyanate, 1-methylcyclohexane 2,4- and/or 2,6-diisocyanate, dicyclohexylmethane 4,4'-, 2,4'- and/or 2,2'-diisocyanate (H12MDI), diphenylmethane 2,2'-, 2,4'- and/or 4,4'-diisocyanate (MDI), naphthylene 1,5-diisocyanate (NDI), tolylene 2,4- and/or 2,6-diisocyanate (TDI), diphenylmethane diisocyanate, 3,3'-dimethyldiphenyl diisocyanate, 1,2-diphenylethane diisocyanate, phenylene diisocyanate, and any combination thereof.

Suitable organic diisocyanates are also 2,4-paraphenylenediisocynate (PPDI) and 2,4-tetramethylenexylenediisocyante (TMXDI).

Diphenylmethane 2,2'-, 2,4'- and/or 4,4'-diisocyanate (MDI), and dicyclohexylmethane 4,4'-, 2,4'- and/or 2,2'-diisocyanate (H12MDI) are preferred. Diphenylmethane 2,2'-, 2,4'- and/or 4,4'-diisocyanate are particularly preferred.

It is also possible that the organic diisocyanate (a) is an isocyanate mixture comprising at least 90% by weight, more preferably at least 95% by weight, further preferably at least 98% by weight 4,4'-diphenylmethane diisocyanates (4,4'-MDI), and the remaining is other diisocyanates.

Generally, the isocyanate is either used as a single isocyanate or a mixture of isocyanates.

Generally, any suitable known component (b) can be used in the context of the present invention. The compounds (b) which are reactive toward isocyanate are preferably polyhydric alcohols, polyesterols (i.e. polyester polyols), polyetherols (i.e. polyether polyols), and/or polycarbonate diols, for which the collective term "polyols" is also usually used. The number average molecular weights (Mn) of these polyols are from 0.5 kg/mol to 8 kg/mol, preferably from 0.6 kg/mol to 5 kg/mol, very preferably from 0.8 kg/mol to 3 kg/mol, in particular 1 kg/mol to 2 kg/mol.

These polyols in addition preferably have only primary hydroxy groups. The polyols are particularly preferably linear hydroxyl-terminated polyols. Owing to the method of production, these polyols often comprise small amounts of nonlinear compounds. They are therefore frequently also referred to as "essentially linear polyols".

The polyol is either used as a single polyol or a mixture of polyols. In another preferred embodiment, the polyol is a mixture of two or more polyols. In one preferred embodiment, it is a mixture of polyester polyols and other polyols such as polyester polyols, polyether polyols and/or polycarbonate diols as compounds (b). Polyester polyols, and a mixture of one or more polyether polyols are particularly preferred.

In case of a mixture of polyols, at least one polyester polyol is used in an amount of more than 40% by weight, preferably more than 60% by weight, more preferably more than 80% by weight, and most preferably more than 90% by weight, based on the total weight of the mixture.

Polyether diols, polyester diols and polycarbonate diols in the invention are those commonly known and frequently used in preparation of thermoplastic polyurethanes.

The polyester diols can be based on dicarboxylic acids having from 2 to 12 carbon atoms, preferably from 4 to 8 carbon atoms, which are generally known for the preparation of polyester diols and polyhydric alcohols.

Examples of polyhydric alcohols are alkanediols having from 2 to 10, preferably from 2 to 6, carbon atoms, e.g. ethanediol, 1,3-propanediol, 1,4-butanediol, 1,5-pentanediol, 1,6-hexanediol, 1,10-decanediol, 2,2-dimethyl-1,3-propanediol, 2-methyl-1,3-propanediol, 1,2-propanediol, 3-methyl-1,5-pentanediol, and dialkylene ether glycols such as diethylene glycol and dipropylene glycol. Another examples of polyhydric alcohols are 2,2-Bis(hydroxymethyl)1,3-propanediol and trimethylolpropane. Depending on the desired properties, the polyhydric alcohols can be used either alone or, if appropriate, in mixtures with one another. To keep the glass transition temperature Tg of the polyol very low, it can be advantageous to use a polyester diol based on branched diols, particularly preferably based on 3-methyl-1,5-pentanediol and 2-methyl-1,3-propandiol. The polyester diol is particularly preferably based on at least two different diols, i.e. polyester diols which are prepared by condensation of dicarboxylic acids with a mixture of at least two different diols. In case of a mixture of diols of which at least one is a branched diol, e.g. 2-methyl-1,3-propane diol, the amount of branched diols is more than 40% by weight, preferably more than 70% by weight, more preferably more than 90% by weight, based on the total weight of the diols mixture.

Preferred dicarboxylic acids are, for example: aliphatic dicarboxylic acids, such as succinic acid, glutaric acid, suberic acid, azelaic acid, sebacic acid and preferably adipic acid and aromatic dicarboxylic acids such as phthalic acid, isophthalic acid and terephthalic acid. The dicarboxylic acids can be used individually or as mixtures, e.g. in the form of a mixture of succinic acid, glutaric acid and adipic acid. Mixtures of aromatic and aliphatic dicarboxylic acids can likewise be used. To prepare the polyesterols, it may be advantageous to use the corresponding dicarboxylic acid derivatives such as dicarboxylic esters having from 1 to 4 carbon atoms in the alcohol radical, dicarboxylic anhydrides or dicarboxylic acid chlorides in place of the dicarboxylic acids. The polyester diol is particularly preferably based on adipic acid. In yet another embodiment Polyester polyols based on ε-caprolactone is preferred.

Suitable polyester polyols, for example, may have a number average molecular weight (Mn) ranging from 0.5 to 3 kg/mol, preferably 0.8 kg/mol to 2.5 kg/mol, more preferably from 1 kg/mol to 2 kg/mol, and in particular 1 kg/mol.

Suitable polyether polyols can be prepared by reacting one or more alkylene oxides having from 2 to 4 carbon atoms in the alkylene radical with a starting material molecule containing two active hydrogen atoms. Typical alkylene oxides are ethylene oxide, 1,2-propylene oxide, epichlorohydrin, and 1,2- and 2,3-butylene oxide. Ethylene oxide and mixtures of 1,2-propylene oxide and ethylene oxide are preferably utilized. The alkylene oxides can be used individually, alternately in succession or as mixtures. The typical starting material molecules are, for example water, amino alcohols such as N-alkyldiethanolamines, and diols, ethyleneglycol, 1,3-propyleneglycol, 1,4-butanediol and 1,6-hexanediol. It is also possible to use mixtures of starting material molecules. Suitable polyether polyols also include hydroxyl group-containing polymerization products of tetrahydrofuran.

Preferably used are hydroxyl group-containing polytetrahydrofuran, and co-polyether polyols of 1,2-proplyene oxide and ethylene oxide in which more than 50 percent of the hydroxyl groups are primary hydroxyl groups, preferably from 60 to 80 percent, and in which at least part of the ethylene oxide is a block in terminal position.

Most preferred polyether polyol is hydroxyl group-containing polytetrahydrofuran having a number average molecular weight in the range from 0.6 to 3 kg/mol, preferably from 0.8 to 2.5 kg/mol, more preferably from 1 kg/mol to 2 kg/mol.

A preferred polyol is a mixture of at least one polyester polyol and at least one polyether polyol. Examples of polyether polyols include but are not limited to those based on generally known starting materials and customary alkylene oxides.

The polyols which can be used in the context of the present invention can either react with isocyanates to produce isocyanate prepolymer or react with isocyanate prepolymers to produce thermoplastic polyurethanes.

Suitable polyols used for reacting with isocyanates to produce an isocyanate prepolymer may have an average functionality>2, preferably between 2.1 and 3, more preferably between 2.1 and 2.7, and most preferably between 2.2 and 2.5. Furthermore, suitable polyols used for reacting with isocyanate prepolymers to produce TPU preferably have an average functionality of from 1.8 to 2.3, preferably from 1.9 to 2.2, in particular 2. The term "functionality" means the number of groups which react with isocyanate under condition of polymerization.

As chain extenders (c), generally known aliphatic, araliphatic, aromatic and/or cycloaliphatic compounds having a molecular weight of from 60 g/mol to 499 g/mol, preferably from 60 g/mol to 400 g/mol can be used, more preferably bifunctional compounds, for example diamines and/or alkane diols having from 2 to 10 carbon atoms in the alkylene radical, in particular 1,2-ethylene diol, 1,4-butanediol, 1,6-hexanediol, 1,3-propanediol, and/or dialkylene-, trialkylene-, tetraalkylene-, pentaalkylene-, hexaalkylene-, heptaalkylene-, octaalkylene-, nonaalkylene- and/or decaalkylene-glycols having from 2 to 8 carbon atoms in alkylene moiety, preferably corresponding oliogopropyleneglycols and/or polypropyleneglycols. It is also possible to use mixtures of the chain extenders. Preference is given to 1,4-butanediol, 1,2-ethylenediol, 1,6-hexanediol or combination thereof as chain extender.

In a preferred embodiment, chain extender (c) is used in an amount of from 2% to 20% by weight, preferably from 5% to 15% by weight, based on the total weight of components (a), (b) and (c).

As chain extender either a single chain extender or a mixture of chain extenders is used.

Suitable catalysts (d), which, in particular, accelerate the reaction between NCO groups of the organic diisocyanates (a) and the polyols (b) and component (c) are tertiary amines which are known and customary in the prior art, for example, triethylamine, dimethylcyclohexylamine, N-methylmorpholine, 2-(dimethylaminoethoxy)ethanol, N,N'-dimethylpiperazine, diazabicyclo[2.2.2]octane and the like, and also, in particular, organic metal compounds such as titanic esters, bismuth carboxylic esters, zinc esters, iron compounds such as iron (III) acetylacetonate, tin compounds, e.g. tin diacetate, tin dioctoate, tin dilaurate or dialkyl tin salts of aliphatic carboxylic acids, e.g. dibutyltin diacetate, dibutyltin dilaurate or the like. In bismuth salts oxidation state of the bismuth is preferably 2 or 3, more preferably 3.

Preferred carboxylic acids of bismuth carboxylic esters have 6 to 14 carbon atoms, more preferred 8 to 12 carbon atoms. Preferred examples of bismuth salts are bismut(III)-neodecanoat, bismut-2-etyhlhexanoat and bismut-octanoat.

The catalysts, if used, are usually used in amounts of from 0.0001 to 0.1 parts by weight per 100 parts by weight of polyols (b). Preference is given to tin catalysts, in particular tin dioctoate.

Apart from catalysts (d), customary auxiliaries (e) and/or additives (f) can be added, if desired, in addition to components (a) to (c).

As auxiliaries (e), for example surface-active substances, flame retardants, nucleating agents, lubricant wax, dyes, pigments, and stabilizers, e.g. against oxidation, hydrolysis, light, heat or discoloration may be used, and as additives (f), for example inorganic and/or organic fillers and reinforcing materials. As hydrolysis inhibitors, preference is given to oligomeric and/or polymeric aliphatic or aromatic carbodiimides. To stabilize thermoplastic polyurethanes against aging, stabilizers can also be added.

Further details regarding optional auxiliaries and additives may be found in the specialist literature, e.g. in Plastics Additive Handbook, 5th edition, H. Zweifel, ed, Hanser Publishers, Munich, 2001.

Besides the stated components a), b), and c) and, if appropriate, d) and e) it is also possible to use chain regulators, usually having a number average molecular weight of 31 g/mol to 3 kg/mol. These chain regulators are compounds which have only one isocyanate-reactive functional group, such as monofunctional alcohols, monofunctional amines and/or monofunctional polyols, for example. Chain regulators of this kind allow a precise rheology to be set, particularly in the case of TPUs. Chain regulators can be used generally in an amount of 0 to 5, preferably 0.1 to 1, part(s) by weight, based on 100 parts by weight of component b), and in terms of definition are included in component (c).

To adjust the hardness of the thermoplastic polyurethane, component (b) which is reactive toward isocyanates and chain extenders (c) can be varied within a relatively wide range of molar ratios. Molar ratios of component (b) to the total of chain extenders (c) to be used from 10:1 to 1:10, in particular from 1:1 to 1:4, have been found to be useful, with hardness of the thermoplastic polyurethane increasing with increasing content of (c).

Suitable thermoplastic polyurethanes preferably have a Shore A hardness of generally less than Shore A 98 in accordance with DIN 53505, more preferred from 60 Shore A to 98 Shore A, even more preferred from 70 Shore A to 95 Shore A, and most preferred from 75 Shore A to 90 Shore A.

Preferably, a thermoplastic polyurethane suitable in the context of the present invention has a density in a range from 1.0 g/cm$^3$ to 1.3 g/cm$^3$. The tensile strength of the thermoplastic polyurethane in accordance with DIN 53504 is more than 10 MPa, preferably more than 15 MPa, particularly preferably more than 20 MPa. The thermoplastic polyurethane suitable in the context of the present invention has an abrasion loss in accordance with DIN 53516 of generally less than 150 mm$^3$, preferably less than 100 mm$^3$.

In general, thermoplastic polyurethanes are prepared by reacting (a) isocyanates with (b) compounds reactive toward isocyanates, usually having a number average molecular weight (Mn) of from 0.5 kg/mol to 10 kg/mol, preferably from 0.5 kg/mol to 5 kg/mol, particularly preferably from 0.8 kg/mol to 3 kg/mol, and (c) chain extenders having a number average molecular weight (Mn) of from 0.05 kg/mol to 0.499 kg/mol, if appropriate in the presence of (d) catalysts and/or (e) conventional additives.

The thermoplastic polyurethane may be produced by two different kinds of processes, namely "one-step" processes and "two-step" process which are known from the state of the art.

Melt-spun elastic fibers based on thermoplastic polyurethanes, in particular thermoplastic polyurethane and a cross linker comprising isocyanate groups, in particular isocyanate prepolymers, are generally known from the state of the art. In the context of the present invention, any suitable melt-spun elastic fiber based on thermoplastic polyurethanes and a cross linker comprising isocyanate groups, in particular isocyanate prepolymers, can be used. Suitable isocyanate prepolymers are described in the following by way of example.

For the purpose of the present invention, the term "isocyanate prepolymer" refers to the reaction product of isocyanates with compounds which are reactive toward isocyanates and have a number average molecular weight in the range from 0.5 kg/mol to 10 kg/mol, preferably from 1 kg/mol to 5 kg/mol. Isocyanate prepolymers are intermediates of the isocyanate polyaddition reaction. In a preferred embodiment the prepolymer has a glass transition temperature Tg below −15° C. and a melting temperature below 70° C. measured by means of DSC in accordance with DIN EN ISO 11357-1.

Suitable isocyanate prepolymers may have preferably a NCO content of from 4 to 27 parts by weight based on the weight of the isocyanate prepolymer. Suitable isocyanate prepolymer according to the invention may be used in the form of a single isocyanate prepolymer or a mixture of isocyanate prepolymers.

Most preferred, the isocyanate prepolymer is the reaction product between diphenylmethane 4,4'-diisocyanate, and/or diphenylmethane 2,2'-diisocyanate, and/or diphenylmethane 2,4'-diisocyanate (MDI) and a polyester polyol based on adipic acid, 2-methyl-1,3-propanediol and 1,4-butanediol, wherein the mole ratio of said polyester polyols to said diisocyanates is 1:1 to 1:5, preferably 1:1.2 to 1:3, more preferably 1:1.5 to 1:2.5, such as 1:2.

In the context of the present invention, the isocyanate prepolymer has an average isocyanate functionality (Fn) of 2 or more than 2, preferably between 2 and 3, more preferably between 2 and 2.7, most preferably between 2 and 2.5.

Additionally, plasticizers can be used in the process for preparing the melt-spun elastic fibers. Suitable plasticizers are generally known from the state of the art, for example from David F. Cadogan and Christopher J. Howick "Plasticizers" in Ullmann's Encyclopedia of Industrial Chemistry 2000, Wiley-VCH, Weinheim.

Suitable plasticizers are $C_{3-15}$, preferably $C_{3-10}$, polycarboxylic acids and their esters with linear or branched $C_{2-30}$, aliphatic alcohols, benzoates, epoxidized vegetable oils, sulfonamides, organophosphates, glycols and its derivatives, and polyethers. Preferred plasticizers are sebacic acid, sebacates, adipic acid, adipates, glutaric acid, glutarates, phthalic acid, phthalates (for example with C8 alcohols), azelaic acid, azelates, maleic acid, maleate, citric acid and its derivatives, see for example WO 2010/125009, incorporated herein by reference. The plasticizers may be used in combination or individually.

Further additives such as for example a polymethylene polyphenyl polyisocyanate may be added in the process for preparing the melt-spun elastic fibers.

For the purpose of the present invention, the term further additives refers to any substance that will be added to the reaction system of said thermoplastic polyurethane, said isocyanate prepolymer and said plasticizer, but not include the said thermoplastic polyurethane, said isocyanate prepolymer and said plasticizer. Usually such substance include the auxiliaries and additives commonly used in this art, as shown in the above under the subtitle "thermoplastic polyurethane".

Processes for the preparation of melt-spun elastic fibers, in particular melt-spun fibers based on thermoplastic polyurethanes are generally known from the state of the art.

The melt-spun elastic fiber based on a thermoplastic polyurethane is generally prepared by reacting the following components:

(1) a thermoplastic polyurethane; and
(2) the isocyanate prepolymer composition.

In a specific embodiment, the process for preparing a melt-spun elastic fiber comprises reacting the following components:

(1) a thermoplastic polyurethane;
(2) the isocyanate prepolymer composition; and
(3) further additives.

According to the present invention, the thermoplastic polyurethane, the isocyanate prepolymer composition and optionally further additives are mixed and the resulting mixture is further treated.

According to one embodiment, the process may include the following steps:

(i) melting a thermoplastic polyurethane in an extruder at a temperature of 180° C. to 220° C.;
(ii) to the molten thermoplastic polyurethane, adding the isocyanate prepolymer composition according to the invention and mixing the resulting mixture to form a melt;
(iii) extruding the melt with a spinneret heated at 190° C. to 230° C. to obtain a melt-spun elastic fiber.

Optionally, the process further includes the following subsequent steps:

(iv) spraying finish oil on the fiber, and the finish oil can be mineral oil and/or silicone oil;
(v) winding up the fiber through a roller at a line speed of 100 to 1000 m/min;
(vi) storing the fibers.

According to step (i), a thermoplastic polyurethane melted in an extruder at a temperature of 180° C. to 220° C. According to the present invention, any extruder can be used. The melting takes place at a temperature of from 180° C. to 220° C., preferably of from 185° C. to 215° C., in particular of from 190° C. to 210° C.

According to step (ii), to the molten thermoplastic polyurethane, the isocyanate prepolymer composition is added and the resulting mixture is mixed to form a melt.

According to step (iii), the melt is extruded with a spinneret heated at 190° C. to 230° C. to obtain a melt-spun elastic fiber.

The process may comprise additional steps (iv) to (vi).

Storing the fibers can be carried out for any suitable length of time under suitable conditions, for example for 15 h at 80° C.

In such a process, the isocyanate prepolymer composition preferably is heated and used at temperature above 20° C. to have better flowability, the temperature of the isocyanate prepolymer composition preferably is lower than 80° C. to avoid undesired reactions, e.g. allophante cross linking.

In one embodiment, the additives and/or plasticizer is added to the thermoplastic polyurethane, the isocyanate prepolymer and/or a mixture of the isocyanate prepolymer and the thermoplastic polyurethane.

For producing the melt-spun elastic fiber based on a thermoplastic polyurethane, the thermoplastic polyurethane is preferably preheated to temperature from 80° C. to 110° C. and kept at this temperature for a period of time, for example 3 hours to dry the thermoplastic polyurethane. Then the thermoplastic polyurethane is put into an extruder to melt the thermoplastic polyurethane. The temperature is preferably set from 160° C. to 280° C., more preferably from 180° C. to 250° C., and even more preferably from 180° C. to 220° C. The isocyanate prepolymers is preferably preheated to temperature from 40° C. to 90° C., more preferred to 50° C. to 80° C., and then is added to the extruder to be mixed with the molten thermoplastic polyurethane. It should be appreciated that the additives and/or plasticizer are introduced in any way described in the above.

According to a further embodiment the present invention therefore is directed to a disposable hygiene article as disclosed above, wherein the melt-spun elastic fiber is prepared by a process comprising the steps
- (i) melting a thermoplastic polyurethane in an extruder at a temperature of 180° C. to 220° C.;
- (ii) to the molten thermoplastic polyurethane, adding a composition comprising a cross linker comprising isocyanate groups and mixing the resulting mixture to form a melt;
- (iii) extruding the melt through a spinneret heated at 190° C. to 230° C. to obtain a melt-spun elastic fiber;
- (iv) spraying finish oil on the fiber, the finish oil being selected from the group consisting of mineral oil and silicone oil;
- (v) winding up the fiber through a roller at a line speed of 100 to 1000 m/min; and
- (vi) storing the fibers.

The melt-spun elastic fibers can be used for any kind of disposable hygiene articles such as for example sanitary napkins and in particular diapers.

According to a further embodiment the present invention therefore is directed to a disposable hygiene article as disclosed above, wherein the disposable hygiene article is a diaper.

Processes for preparing disposable hygiene articles are generally known to the person skilled in the art. According to the present invention, a disposable hygiene article can be prepared by applying the melt-spun elastic fiber to the disposable hygiene article or a part of the disposable hygiene article.

According to another aspect, the present invention is directed to a process for preparing a disposable hygiene article comprising the steps:
- (I) providing a melt-spun elastic fiber;
- (II) applying the melt-spun elastic fiber to a disposable hygiene article or a part which is used to prepare the disposable hygiene article.

Step (i) preferably comprises steps (i) to (iii), in particular steps (i) to (vi). Therefore, according to a further embodiment, the present invention is directed to a process for preparing a disposable hygiene article comprising the steps:
- (I) providing a melt-spun elastic fiber, comprising
  - (i) melting a thermoplastic polyurethane in an extruder at a temperature of 180° C. to 220° C.;
  - (ii) to the molten thermoplastic polyurethane, adding a composition comprising a cross linker comprising isocyanate groups and mixing the resulting mixture to form a melt;
  - (iii) extruding the melt through a spinneret heated at 190° C. to 230° C. to obtain a melt-spun elastic fiber;
- (II) applying the melt-spun elastic fiber to a disposable hygiene article or a part which is used to prepare the disposable hygiene article.

In particular, the present invention is directed to a process for preparing a disposable hygiene article comprising the steps:
- (I) providing a melt-spun elastic fiber, comprising
  - (i) melting a thermoplastic polyurethane in an extruder at a temperature of 180° C. to 220° C.;
  - (ii) to the molten thermoplastic polyurethane, adding a composition comprising a cross linker comprising isocyanate groups and mixing the resulting mixture to form a melt;
  - (iii) extruding the melt through a spinneret heated at 190° C. to 230° C. to obtain a melt-spun elastic fiber;
  - (iv) spraying finish oil on the fiber, the finish oil being selected from the group consisting of mineral oil and silicone oil;
  - (v) winding up the fiber through a roller at a line speed of 100 to 1000 m/min; and
  - (vi) storing the fibers;
- (II) applying the melt-spun elastic fiber to a disposable hygiene article or a part which is used to prepare the disposable hygiene article.

It is generally possible to apply the fiber according to step (II) by any known method for example by using an adhesive. In case an adhesive is used, the adhesive is generally applied to the disposable hygiene article or a part of the disposable hygiene article and the fiber is applied subsequently. Finally, the respective part covered by the adhesive is covered by an additional layer, preferably a paper layer.

Alternatively, it is possible to apply the melt-spun elastic fiber by melt bonding. According to this embodiment, the fiber is heated in order to make it adhesive and subsequently the preheated fiber is applied to the disposable hygiene article or the part of the disposable hygiene article. This allows to avoid an additional adhesive and makes the preparation process more efficient and reduces costs.

Preferred melt-spun elastic fibers are disclosed above.

Therefore, according to a further embodiment, the present invention is directed to a process for preparing a disposable hygiene article as disclosed above, wherein the melt-spun elastic fiber is based on a thermoplastic polyurethane.

According to another embodiment, the present invention is directed to a process for preparing a disposable hygiene article as disclosed above, wherein the melt-spun elastic fiber has a linear density in the range of from 200D to 800D.

According to a further embodiment, the present invention is directed to a process for preparing a disposable hygiene article as disclosed above, wherein the melt-spun elastic fiber is applied to the disposable hygiene article or the part which is used to prepare the disposable hygiene article by melt bonding the fiber to the surface of the disposable hygiene article or the part which is used to prepare the disposable hygiene article.

Preparation processes for preparing disposable hygiene articles are generally known. The process for applying a melt-spun elastic fiber in the process for preparing a diaper is described in more detail by way of example without limiting the invention.

Generally, a disposable hygiene article, in particular a disposable diaper consists of an absorbent pad sandwiched between two sheets of nonwoven fabric. The pad is specially designed to absorb and retain body fluids, and the nonwoven fabric gives the diaper a comfortable shape and helps prevent leakage. These diapers are made by a multi-step process in which the absorbent pad is first vacuum-formed, then attached to a permeable top sheet and impermeable bottom sheet. Elastic fibers are attached to the sheets to gather the edges of the diaper into the proper shape.

According to one embodiment of the present invention, a melt-spun elastic fiber can be applied to the flap part of the legs and to the cuff part of a disposable diaper. The cuff part in the diaper primarily prevents the liquid discharge of the diaper from leaking out thereof, and the flap part of the legs secondly prevents the leakage of liquid discharge. Those two parts, the flap part and cuff part, have direct influence on the wearing comfort as they are closely attached to the skin. If an elastic yarn used is too tight, the wearing comfort deteriorates and causing a red mark around the legs, while if too loose, the liquid discharge may leak out of diapers. Therefore, in order to achieve both the wearing comfort and functionality, an elastic yarn is required to have the physical properties that are flexible enough to extend easily when being pulled, and that at the same time are closely attached to the skin all the time. The properties relates closely to power retention of an elastic fiber.

According to another aspect, the present invention is directed to the use of a melt-spun elastic fiber in a preparation process for preparing a disposable hygiene article.

The present invention includes the following embodiments, wherein these include the specific combinations of embodiments as indicated by the respective interdependencies defined therein.

1. A disposable hygiene article comprising a melt-spun elastic fiber.
2. The disposable hygiene article according to embodiment 1, wherein the melt-spun elastic fiber has no signal in the range of from 1620 cm$^{-1}$ to 1640 cm$^{-1}$ in an IR-spectrum.
3. The disposable hygiene article according to embodiment 1 or 2, wherein the melt-spun elastic fiber is based on a thermoplastic polyurethane.
4. The disposable hygiene article according to any one of embodiments 1 to 3, wherein the melt-spun elastic fiber has a linear density in the range of from 200D to 800D.
5. The disposable hygiene article according to any one of embodiments 1 to 3, wherein the melt-spun elastic fiber has a linear density in the range of from 800D to 1000D.
6. The disposable hygiene article according to any one of embodiments 3 to 5, wherein the thermoplastic polyurethane has a shore hardness in the range of from 60 A to 98 A, determined according to DIN 53505.
7. The disposable hygiene article according to any one of embodiments 1 to 6, wherein the melt-spun elastic fiber has a kofler melting temperature in the range of from 25° C. to 230° C.
8. The disposable hygiene article according to any one of embodiments 1 to 7, wherein the melt-spun elastic fiber is based on a thermoplastic polyurethane and a cross linker comprising isocyanate groups.
9. The disposable hygiene article according to any one of embodiments 1 to 8, wherein the melt-spun elastic fiber is prepared by a process comprising the steps
   (i) melting a thermoplastic polyurethane in an extruder at a temperature of 180° C. to 220° C.;
   (ii) to the molten thermoplastic polyurethane, adding a composition comprising a cross linker comprising isocyanate groups and mixing the resulting mixture to form a melt;
   (iii) extruding the melt through a spinneret heated at 190° C. to 230° C. to obtain a melt-spun elastic fiber.
10. The disposable hygiene article according to any one of embodiments 1 to 8, wherein the melt-spun elastic fiber is prepared by a process comprising the steps
   (i) melting a thermoplastic polyurethane in an extruder at a temperature of 180° C. to 220° C.;
   (ii) to the molten thermoplastic polyurethane, adding a composition comprising a cross linker comprising isocyanate groups and mixing the resulting mixture to form a melt;
   (iii) extruding the melt through a spinneret heated at 190° C. to 230° C. to obtain a melt-spun elastic fiber;
   (iv) spraying finish oil on the fiber, the finish oil being selected from the group consisting of mineral oil and silicone oil;
   (v) winding up the fiber through a roller at a line speed of 100 to 1000 m/min; and
   (vi) storing the fibers.
11. The disposable hygiene article according to any one of embodiments 1 to 10, wherein the disposable hygiene article is a diaper.
12. Process for preparing a disposable hygiene article comprising the steps:
   (I) providing a melt-spun elastic fiber;
   (II) applying the melt-spun elastic fiber to a disposable hygiene article or a part which is used to prepare the disposable hygiene article.
13. The process according to embodiment 12, wherein the melt-spun elastic fiber has no signal in the range of from 1620 cm$^{-1}$ to 1640 cm$^{-1}$ in an IR-spectrum.
14. The process according to embodiment 12 or 13, wherein the melt-spun elastic fiber is based on a thermoplastic polyurethane.
15. The process according to any one of embodiments 12 to 14, wherein the melt-spun elastic fiber has a linear density in the range of from 200D to 800D.
16. The process according to any one of embodiments 12 to 14, wherein the melt-spun elastic fiber has a linear density in the range of from 800D to 1000D.
17. The process according to any one of embodiments 12 to 16, wherein the melt-spun elastic fiber is applied to the disposable hygiene article or the part which is used to prepare the disposable hygiene article by melt bonding the fiber to the surface of the disposable hygiene article or the part which is used to prepare the disposable hygiene article.
18. Use of a melt-spun elastic fiber in a preparation process for preparing a disposable hygiene article.
19. A disposable hygiene article comprising a melt-spun elastic fiber.
20. The disposable hygiene article according to embodiment 19, wherein the melt-spun elastic fiber is based on a thermoplastic polyurethane.
21. The disposable hygiene article according to embodiment 19 or 20, wherein the melt-spun elastic fiber has a linear density in the range of from 200D to 800D.
22. The disposable hygiene article according to embodiment 20 or 21, wherein the thermoplastic polyurethane has a shore hardness in the range of from 60 A to 98 A, determined according to DIN 53505.
23. The disposable hygiene article according to any one of embodiments 19 to 22, wherein the melt-spun elastic fiber has a kofler melting temperature in the range of from 25° C. to 230° C.
24. The disposable hygiene article according to any one of embodiments 19 to 23, wherein the melt-spun elastic fiber is based on a thermoplastic polyurethane and a cross linker comprising isocyanate groups.
25. The disposable hygiene article according to any one of embodiments 19 to 24, wherein the melt-spun elastic fiber is prepared by a process comprising the steps (i) melting a thermoplastic polyurethane in an extruder at a temperature of 180° C. to 220° C.;
(ii) to the molten thermoplastic polyurethane, adding a composition comprising a cross linker comprising isocyanate groups and mixing the resulting mixture to form a melt;
(iii) extruding the melt through a spinneret heated at 190° C. to 230° C. to obtain a melt-spun elastic fiber;
(iv) spraying finish oil on the fiber, the finish oil being selected from the group consisting of mineral oil and silicone oil;
(v) winding up the fiber through a roller at a line speed of 100 to 1000 m/min; and
(vi) storing the fibers.
26. The disposable hygiene article according to any one of embodiments 19 to 25, wherein the disposable hygiene article is a diaper.
27. Process for preparing a disposable hygiene article comprising the steps:
(I) providing a melt-spun elastic fiber;
(II) applying the melt-spun elastic fiber to a disposable hygiene article or a part which is used to prepare the disposable hygiene article.
28. The process according to embodiment 27, wherein the melt-spun elastic fiber is based on a thermoplastic polyurethane.
29. The process according to embodiment 27 or 28, wherein the melt-spun elastic fiber has a linear density in the range of from 200D to 800D.
30. The process according to any one of embodiments 27 to 29, wherein the melt-spun elastic fiber is applied to the disposable hygiene article or the part which is used to prepare the disposable hygiene article by melt bonding the fiber to the surface of the disposable hygiene article or the part which is used to prepare the disposable hygiene article.
31. Use of a melt-spun elastic fiber in a preparation process for preparing a disposable hygiene article.

Examples will be used below to illustrate the invention. The following examples are intended to illustrate the invention without limiting.

EXAMPLES

The following materials were used in the examples:
TPU-1: Thermoplastic polyurethane with Shore 80A hardness, based on 1,4-butanediol, 4,4'-diphenylmethane diisocyanate and polyesterdiol with number molecular weight 2 kg/mol. The said polyesterdiol is based on adipic acid, 2-methyl-1,3-propanediol and 1,4-butanediol, with the latter two in the mass ratio of 1:1.
TPU-2: Thermoplastic polyurethane with Shore 85A hardness, based on 1,6-hexanediol, 4,4'-diphenylmethane diisocyanate and polyesterdiol with number molecular weight 1 kg/mol. The said polyesterdiol is based on adipic acid, and 1,4-butanediol.
Prepolymer-1: based on 4,4'-diphenylmethane diisocyanate (2 mol) and polyesterdiol (1 mol) with number molecular weight 2 kg/mol. The said polyesterdiol is based on adipic acid, 2-methyl-1,3-propanediol and 1,4-butanediol, with the latter two in the mass ratio of 1:1.
Prepolymer-2: based on 4,4'-diphenylmethane diisocyanate (2 mol) and polytetramethylene ether glycol (1 mol) with number molecular weight 1 kg/mol.

1. General Procedure

In these examples, melt-spun elastic fiber were produced by the following process:
(1) melting a thermoplastic polyurethane in a single screw extruder at a temperature of 200° C. or as indicated;
(2) adding the prepolymer into the molten TPU from step (1), and mixing them to form a melt;
(3) extruding the melt through a spinneret which is heated at 200° C. or as indicated to obtain a melt-spun elastic fiber;
(4) spraying finish oil on the fiber, and the finish oils was silicone oil;
(5) winding up the fiber through a roller at a line speed of 500 m/min;
(6) storing the fibers for 15 h at 80° C. for better comparability.

2. Example 1

880 g TPU-1 was melted at 200° C. through a single screw extruder, and 120 g prepolymer-1 was added to the TPU melt and mixed. The melt was extruded through a spinneret with temperature at 195° C.

3. Example 2

930 g TPU-2 was melted at 200° C. through a single screw extruder, and 70 g prepolymer-2 was added to the TPU melt and mixed. The melt was extruded through a spinneret with temperature at 210° C.

TABLE 1

| Kofler melt temperature | | | |
|---|---|---|---|
| | Examples | | |
| | 1 | 2 | Dry spun spandex[b] |
| Kofler melt temperature (° C.)[a] | 205 | 190 | 240 |

[a] the kofler melting temperature refer to the temperature that the fiber changes from solid to liquid after it was placed on the hot metal strip of the kofler bench for 1 min.
[b] a dry spun spandex bought from market: creora® Comfort 540dtex.

4. Comparison of Physical Properties

The test results in table 1 show that the melt spun elastic fibers have much lower melting temperature of dry spun spandex, the lower melting temperature allow the melt spun elastic fiber directly bond to the substrate by heating without any adhesives. In the same time, the mechanical properties of a melt-spun elastic fiber based on a thermoplastic polyurethane with a shore hardness of 80 A and an isocyanate cross linker (Example 1) were compared to the mechanical properties of a commercially available dry spun spandex. The results are summarized in table 2. The tensile strength and the elongation at break of the two elastic fibers are quite similar, this indicates that the melt spun elastic fiber (Example 1) is one of suitable candidates to replace the commercially available dry spun spandex in diaper application.

TABLE 2

| Mechanical properties | | | |
|---|---|---|---|
| | | Examples | |
| | Standard | 1 | Dry spun spandex[a] |
| Tensile strength (cN/D) | DIN 53834 | 1.2 | 1.0 |
| Elongation at break (%) | DIN 53834 | 603 | 634 |

[a] a dry spun spandex bought from market: creora® Comfort 540dtex.

5. Suitable Conditions for Measuring IR Spectra

If not noted otherwise, the wave length refers to a FT IR-spectrum measured at a wave length in the range of 4000 to 600 $cm^{-1}$. Generally, an IR spectrum is measured with a resolution of 4 $cm^{-1}$. A BRUKER tensor 27 can be used (background scan time: 16 scans, sample scan time: 16 scans).

The invention claimed is:

1. A disposable hygiene article, comprising a melt-spun elastic fiber based on a thermoplastic polyurethane and a cross linker comprising isocyanate groups, wherein the thermoplastic polyurethane has a shore hardness of from 60A to 98A, determined according to DIN 53505.

2. The disposable hygiene article according to claim 1, wherein the melt-spun elastic fiber has no signal in the range of from 1620 $cm^{-1}$ to 1640 $cm^{-1}$ in an IR-spectrum.

3. The disposable hygiene article according to claim 1, wherein the melt-spun elastic fiber has a linear density of from 200D to 800D.

4. The disposable hygiene article according to claim 1, wherein the melt-spun elastic fiber has a linear density of from 800D to 1000D.

5. The disposable hygiene article according to claim 1, wherein the thermoplastic polyurethane has a shore hardness of from 70 A to 98 A, determined according to DIN 53505.

6. The disposable hygiene article according to claim 1, wherein the melt-spun elastic fiber has a kofler melting temperature of from 25° C. to 230° C.

7. The disposable hygiene article according to claim 1, wherein the melt-spun elastic fiber is prepared by a process comprising:
   (i) melting a thermoplastic polyurethane in an extruder at a temperature of 180° C. to 220° C. to obtain a molten thermoplastic polyurethane;
   (ii) to the molten thermoplastic polyurethane, adding a composition comprising a cross linker comprising isocyanate groups and mixing the resulting mixture to form a melt; and
   (iii) extruding the melt through a spinneret heated at 190° C. to 230° C. to obtain a melt-spun elastic fiber.

8. The disposable hygiene article according to claim 1, wherein the melt-spun elastic fiber is prepared by a process comprising:
   (i) melting a thermoplastic polyurethane in an extruder at a temperature of 180° C. to 220° C. to obtain a molten thermoplastic polyurethane;
   (ii) to the molten thermoplastic polyurethane, adding a composition comprising a cross linker comprising isocyanate groups and mixing the resulting mixture to form a melt;
   (iii) extruding the melt through a spinneret heated at 190° C. to 230° C. to obtain a melt-spun elastic fiber;
   (iv) spraying finish oil on the melt-spun elastic fiber, the finish oil being selected from the group consisting of mineral oil, silicone oil, and a combination thereof;
   (v) winding up the melt-spun elastic fiber through a roller at a line speed of 100 to 1000 m/min; and
   (vi) storing the melt-spun elastic fiber.

9. The disposable hygiene article according to claim 1, wherein the disposable hygiene article is a diaper.

10. A process for preparing a disposable hygiene article, the process comprising applying a melt-spun elastic fiber to a disposable hygiene article or a part which is used to prepare the disposable hygiene article, wherein:
   the melt-spun elastic fiber is based on a thermoplastic polyurethane and a cross linker comprising isocyanate groups; and
   the thermoplastic polyurethane has a shore hardness of from 60A to 98A, determined according to DIN 53505.

11. The process according to claim 10, wherein the melt-spun elastic fiber has no signal in the range of from 1620 $cm^{-1}$ to 1640 $cm^{-1}$ in an IR-spectrum.

12. The process according to claim 10, wherein the melt-spun elastic fiber has a linear density of from 200D to 800D.

13. The process according to claim 10, wherein the melt-spun elastic fiber has a linear density of from 800D to 1000D.

14. The process according to claim 10, wherein the melt-spun elastic fiber is applied to the disposable hygiene article or the part which is used to prepare the disposable hygiene article by melt bonding the fiber to the surface of the disposable hygiene article or the part which is used to prepare the disposable hygiene article.

* * * * *

UNITED STATES PATENT AND TRADEMARK OFFICE
CERTIFICATE OF CORRECTION

PATENT NO. : 10,369,059 B2
APPLICATION NO. : 15/029135
DATED : August 6, 2019
INVENTOR(S) : Bin-Erik Chen Page 1 of 1

It is certified that error appears in the above-identified patent and that said Letters Patent is hereby corrected as shown below:

In the Specification

Column 7, Lines 39-40, "oliogopropyleneglycols" should read -- oligopropyleneglycols --

Column 7, Line 60, "dioctoate" should read -- dioctanoate --

Column 7, Lines 66-67, "bismuth(III)-neodecanoat" should read -- bismuth(III)-neodecanoate --

Column 7, Line 67, "bismut-2-etyhlhexanoat" should read -- bismuth-2- ethylhexanoate --

Column 7, Line 67, "bismut-octanoat." should read -- bismuth-octanoate. --

Column 8, Line 4, "dioctoate." should read -- dioctanoate. --

Column 10, Line 63, "allophante" should read -- allophanate --

Signed and Sealed this
Twenty-eighth Day of April, 2020

Andrei Iancu
*Director of the United States Patent and Trademark Office*